(12) United States Patent
Heinemann et al.

(10) Patent No.: US 6,589,974 B1
(45) Date of Patent: Jul. 8, 2003

(54) PYRAZOLYL BENZYL ETHER DERIVATIVES CONTAINING A FLUOROMETHOXYIMINO GROUP AND USE THEREOF AS PESTICIDES

(75) Inventors: Ulrich Heinemann, Leichlingen (DE); Herbert Gayer, Monheim (DE); Peter Gerdes, Aachen (DE); Bernd-Wieland Krüger, Bergisch Gladbach (DE); Fritz Maurer, Monheim (DE); Martin Vaupel, Leichlingen (DE); Astrid Mauler-Machnik, Leichlingen (DE); Ulrike Wachendorff-Neumann, Neuwied (DE); Gerd Hänssler, Leverkusen (DE); Karl-Heinz Kuck, Langenfeld (DE); Peter Lösel, Leverkusen (DE); Christoph Erdelen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,888

(22) PCT Filed: Dec. 11, 2000

(86) PCT No.: PCT/EP00/12481

§ 371 (c)(1),
(2), (4) Date: Oct. 29, 2002

(87) PCT Pub. No.: WO01/46154

PCT Pub. Date: Jun. 28, 2001

(30) Foreign Application Priority Data

Dec. 22, 1999 (DE) .......................... 199 62 012
Jul. 13, 2000 (DE) .......................... 100 34 129

(51) Int. Cl.$^7$ .............................................. A61K 31/415
(52) U.S. Cl. ........................................................ 514/407
(58) Field of Search ........................ 548/371.1; 514/407

(56) References Cited

U.S. PATENT DOCUMENTS

| | | | |
|---|---|---|---|
| 5,583,249 A | 12/1996 | Pfifner et al. | 560/35 |
| 5,710,314 A | 1/1998 | Pfiffner et al. | 560/60 |
| 5,935,908 A | 8/1999 | Farooq et al. | 504/281 |
| 6,031,110 A * | 2/2000 | Kirstgen et al. | 548/370.1 |
| 6,306,855 B1 | 10/2001 | Heinemann et al. | 514/241 |
| 2002/0028811 A1 | 3/2002 | Heinemann et al. | 514/241 |

FOREIGN PATENT DOCUMENTS

| | | |
|---|---|---|
| DE | 44 24 788 | 6/1995 |
| EP | 0 757 042 | 2/1997 |
| WO | 99/33812 | 7/1999 |

OTHER PUBLICATIONS

Chem. Pharm. Bull. 19(7), (month unavailable) 1971, pp. 1389–1394, "Studies of Acetylenic Compounds. LVI,$^{1,2)}$ Syntheses of 4–Isoxazolin–3–one and 1–Phenyl–3–hydroxypyrazoles", Norio Nakamura, Yukichi Kishida and Noboru Ishida.

* cited by examiner

*Primary Examiner*—Robert W. Ramsuer
(74) *Attorney, Agent, or Firm*—Richard E. L. Henderson; Raymond J. Harmuth

(57) ABSTRACT

The invention relates to novel pyrazolyl benzyl ethers, to a plurality of processes for their preparation and to their use for controlling harmful organisms.

8 Claims, No Drawings

PYRAZOLYL BENZYL ETHER DERIVATIVES CONTAINING A FLUOROMETHOXYIMINO GROUP AND USE THEREOF AS PESTICIDES

The invention relates to novel pyrazolyl benzyl ethers, to a plurality of processes for their preparation and to their use for controlling harmful organisms.

Certain compounds having a similar substitution pattern, and their fungicidal action, are already known (WO 98/55461, WO 97/07103, WO 96/10556, WO 96/06072, WO 99/33812, DE-A 4424788). However, the activity of these prior-art compounds is, in particular at low application rates and concentrations, not entirely satisfactory in all areas of use.

This invention now provides the novel pyrazolyl benzyl ethers of the general formula (I)

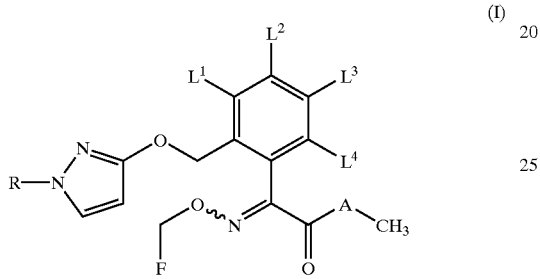

in which
  A represents oxygen or —NH—,
  R represents in each case optionally substituted alkyl, cycloalkyl or aryl,
  $L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

In the definitions, the saturated or unsaturated hydrocarbon chains, such as alkyl, alkanediyl, alkenyl or alkinyl, are in each case straight-chain or branched, including in combination with heteroatoms, such as, for example, in alkoxy, alkylthio or alkylamino.

Unless indicated otherwise, preference is given to hydrocarbon chains having 1 to 6 carbon atoms.

Aryl represents aromatic mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated and also aromatic cyclic compounds in which at least one ring member is a heteroatom, i.e. an atom different from carbon. If the ring contains a plurality of heteroatoms, these can be identical or different. If the ring contains a plurality of oxygen atoms, these are not adjacent. Preferred heteroatoms are oxygen, nitrogen and sulphur. If appropriate, the cyclic compounds form, together with further carbocyclic or heterocyclic fused-on or bridged rings, a polycyclic ring system. Preference is given to mono- or bicyclic ring systems, in particular to mono- or bicyclic aromatic ring systems. A polycyclic ring system can be attached via the heterocyclic ring or via a fused-on carbocyclic ring.

Cycloalkyl represents saturated carbocyclic compounds which, if appropriate, form a polycyclic ring system together with further carbocyclic fused-on or bridged rings.

Furthermore, it has been found that the novel pyrazolyl benzyl ethers of the general formula (I) are obtained when
a) benzyl halides of the formula (II)

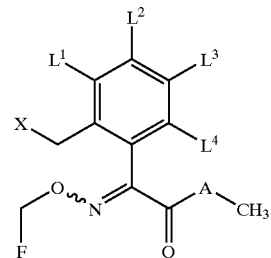

in which
  A, $L^1$, $L^2$, $L^3$ and $L^4$ are as defined above and
  X represents halogen,
are reacted with a substituted pyrazolone of the general formula (III),

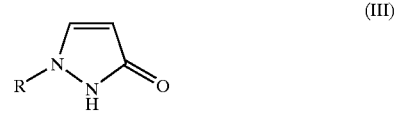

in which
  R is as defined above, if appropriate in the presence of a diluent and if appropriate in the presence of an acid acceptor, or when
b) pyrazolyl benzyl ethers of the formula (I) where A is oxygen are reacted with methylamine, if appropriate in the presence of a diluent.

Finally, it has been found that the novel pyrazolyl benzyl ethers of the general formula (I) are highly active against harmful organisms and exhibit in particular very strong fungicidal and insecticidal action.

The active-compounds according to the invention may also, at certain concentrations and application rates, exhibit activity against plant pests.

If appropriate, the compounds according to the invention can be present as mixtures of different possible isomeric forms, in particular of stereoisomers, such as, for example, E and Z. What is claimed are both the E and the Z isomers, and any mixtures of these isomers.

The invention preferably provides compounds of the formula (I) in which
  A represents oxygen or —NH—,
  R represents alkyl having 1 to 8 carbon atoms,
    represents cycloalkyl having 3 to 7 carbon atoms which is optionally mono- or disubstituted by halogen, alkyl or hydroxyl;
    or represents phenyl or naphthyl, each of which is optionally mono- to tetrasubstitued by identical of different substituents, where the possible substituents are preferably selected from the list below:
      halogen, cyano, nitro, amino, hydroxyl, formyl, carboxyl, carbamoyl, thiocarbamoyl;
      in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
      in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl, having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which radicals is optionally mono- to tetrasubstituted by identical or different substituents from the group consisting of fluorine, chlorine, oxo, methyl, trifluoromethyl and ethyl;

or a group

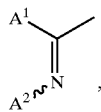

in which
A$^1$ represents hydrogen, hydroxyl or alkyl having 1 to 4 carbon atoms or cycloalkyl having 3 to 6 carbon atoms and A$^2$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms, and phenyl, phenoxy, phenylthio, benzoyl, benzoylethenyl, cinnamoyl, heterocyclyl or phenylalkyl, phenylalkyloxy, phenylalkylthio, or heterocyclylalkyl having in each case 1 to 3 carbon atoms in the respective alkyl moieties, each of which radicals is optionally mono- to trisubstituted in the ring moiety by halogen and/or straight-chain or branched alkyl or alkoxy having 1 to 4 carbon atoms, L$^1$, L$^2$, L$^3$ and L$^4$ are identical or different and independently of one another each represents hydrogen, halogen, cyano, nitro, or represents alkyl, alkoxy, alkylthio, alkylsulphinyl or alkylsulphonyl having in each case 1 to 6 carbon atoms, each of which radicals is optionally substituted by 1 to 5 halogen atoms.

The invention relates in particular to compounds of the formula (I) in which

A represents oxygen or —NH—,
R represents methyl, ethyl, n- or i-propyl, n-, i-, s- or t-butyl, pentyl or hexyl, or represents cyclopentyl or cyclohexyl, each of which is optionally mono- or disubstituted by fluorine, chlorine, methyl, ethyl or hydroxyl;

or represents phenyl or naphthyl, each of which is optionally mono- to tetrasubstituted by identical or different substituents, where the possible substituents are preferably selected from the list below:

fluorine, chlorine, bromine, iodine, cyano, nitro, amino, hydroxyl, formyl, carboxyl, carbamoyl, thiocarbamoyl, methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl, methoxy, ethoxy, n- or i-propoxy, methoxymethyl, ethoxymethyl, methylthio, ethylthio, n- or i-propylthio, methylsulphinyl, ethylsulphinyl, methylsulphonyl or ethylsulphonyl, methylthiomethyl, ethylthiomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl, in each case doubly attached propanediyl, ethyleneoxy, methylenedioxy, ethylenedioxy, each of which is optionally mono- to tetrasubstituted by identical or different substituents from the group consisting of fluorine, chlorine, oxo, methyl and trifluoromethyl, or a grouping

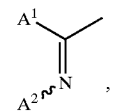

where
A$^1$ represents hydrogen, methyl or hydroxyl and
A$^2$ represents hydroxyl, methoxy, ethoxy, amino, methylamino, phenyl, benzyl or hydroxyethyl, and phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the ring moiety by halogen and/or straight-chain or branched alkyl or alkoxy having 1 to 4 carbon atoms, and L$^1$, L$^2$, L$^3$ and L$^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

The invention relates in particular to compounds of the formula (I) in which

A represents oxygen or —NH—, or

R represents phenyl which is optionally mono- to tetra-substituted by identical or different substituents, where the possible substituents are preferably selected from the list below:
cyano, fluorine, chlorine, bromine, methyl, ethyl, n- or i-propyl, n-, i-, s- or t-butyl, trifluoromethyl, $L^1$ and $L^3$ represent hydrogen and $L^2$ and $L^4$ independently of one another represent hydrogen or methyl.

In a further very particularly preferred group of compounds $L^1$ and $L^3$ represent hydrogen and $L^2$ and $L^4$ independently of one another represent hydrogen or methyl.

The general or preferred radical definitions given above apply both to the end products of the formula (I) and, correspondingly, to the starting materials or intermediates required in each case for the preparation.

The radical definitions given in the respective combinations or preferred combinations of radicals for these individual radicals are, independently of the combination of radicals given in each case, also replaced by any radical definitions of other preferred ranges.

The formula (II) provides a general definition of the benzyl halides required as starting materials for carrying out the process a) according to the invention. In this formula (II), A, $L^1$, $L^2$, $L^3$ and $L^4$ preferably or in particular have those meanings which have already been mentioned in connection with the description of the compounds of the formula (I) according to the invention as being preferred or as being particularly preferred for A, $L^1$, $L^2$, $L^3$ and $L^4$. X represents halogen, preferably chlorine or bromine.

The starting materials of the formula (II) are known and can be prepared by known processes (compare, for example, WO 97/07103, WO 96/10556, WO 96/06072).

The formula (III) provides a general definition of the pyrazolones furthermore required as starting materials for carrying out the process a) according to the invention. In this formula (III), R preferably or in particular has that meaning which has already been given in connection with the description of the compounds of the formula (I) according to the invention as being preferred or as being particularly preferred for R.

The starting materials of the formula (III) are known and/or can be prepared by known methods (compare, for example, Chem. Pharm. Bull. 19, 1389 (1971)).

The pyrazolyl benzyl ethers of the formula (I) where A is oxygen required as starting materials for carrying out the process b) according to the invention are compounds according to the invention and can be obtained according to process a).

The methylamine furthermore required as starting material for carrying out the process b) according to the invention is a generally customary chemical for synthesis.

Suitable diluents for carrying out processes a) and b) according to the invention are all inert organic solvents. These preferably include aliphatic, alicyclic or aromatic hydrocarbons, such as, for example petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl t-butyl ether, methyl-t-amyl ether, dioxane, tetrahydrofuran, 1,2-dimethoxyethane, 1,2-diethoxyethane or anisol; ketones, such as, for example, acetone, butanone, methyl isobutyl ketone or cyclohexanone; nitriles, such as, for example, acetonitrile, propionitrile, n- or i-butyronitrile or benzonitrile; amides, such as, for example, N,N-dimethylformamide, N,N-dimethylacetamide, N-methylformanilide, N-methylpyrrolidone or hexamethylphosphorictriamide; esters, such as, for example, methyl acetate, or ethyl acetate; sulphoxides, such as, for example, dimethyl sulphoxide; sulphones, such as, for example, sulpholane, alcohols, such as, for example, methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process a) according to the invention is, if appropriate, carried out in the presence of a suitable acid acceptor. Suitable acid acceptors are all customary inorganic or organic bases. These preferably include alkaline earth metal or alkali metal hydrides, hydroxides or amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as, for example, trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloandecene (DBU).

When carrying out the process a) according to the invention, the reaction temperatures can be varied within a relatively wide range. In general, the process is carried out at temperatures of from −20° C. to 100° C., preferably at temperatures of from −10° C. to 80° C.

When carrying out the process b) according to the invention, the temperatures can be varied within a relatively wide range. In general, the process is carried out at temperatures of from −20° C. to 100° C., preferably temperatures of from −10 C. to 50° C.

For carrying out the process a) according to the invention for preparing compounds of the formula (I), in general from 0.5 to 15 mol, preferably from 0.8 to 8 mol, of substituted pyrazolone of the formula (III) are employed per mole of the benzyl halide of the formula (II).

For carrying out the process b) according to the invention for preparing compounds of the formula (I), in general from 1 to 50 mol, preferably from 1 to 10 mol, of methylamine are employed per mole of the pyrazolyl benzyl ether of the formula (I) where A is oxygen.

The processes a) and b) according to the invention are generally carried out under atmospheric pressure. However, it is also possible to operate under elevated or reduced pressure—in general between 0.1 bar and 10 bar.

The practice of the reaction and the work-up and isolation of the reaction products are carried out according to generally customary methods (compare also the Preparation Examples).

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae*; and Pseudocercosporella species, such as, for example, *Pseudocercosporella herpotrichoides.*

The fact that the active compounds are well tolerated by plants at the concentrations required for controlling plant diseases permits the treatment of above-ground parts of plants, of propagation stock and seeds, and of the soil.

The active compounds according to the invention can be employed particularly successfully for controlling cereal diseases, such as, for example, against Erysiphe, Leptosphaeria or Puccinia species, diseases in fruit and vegetable growing and viticulture, such as, for example, against Alternaria, *Venturia Sphaerotheca* and Plasmopara species, or rice diseases, such as, for example, against Pyricularia.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

The active compounds, being tolerated well by plants and having favourable homeotherm toxicity, are suitable for controlling animal pests, in particular insects, arachnids and nematodes, encountered in agriculture, in forests, in the protection of stored products and materials and in the hygiene sector. They can preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus*, Gryllotalpa spp., *Locusta migratoria migratorioides*, Melanoplus spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, Reticulitermes spp.

From the order of the Phthiraptera, for example, *Pediculus humanus corporis*, Haematopinus spp., Linognathus spp., Trichodectes spp. and Damalinea spp.

From the order of the Thysanoptera, for example, *Hercinothrips femoralis, Thrips tabaci, Thrips palmi* and *Frankliniella occidentalis.*

From the order of the Heteroptera, for example, Eurygaster spp., *Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera devastatrix*, Pemphigus spp., *Macrosiphum avenae*, Myzus spp., *Phorodon humuli, Rhopalosiphum padi*, Empoasca spp., *Euscelis bilobatus, Nephotettix* cincticeps, Lecanium corni, Saissetia oleae, Laodelphax striatellus, Nilaparvata lugens, Aonidiella aurantii, Aspidiotus hederae, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Mamestra brassicae, Panolis flammea,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana,* Cnaphalocerus spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon soistitialis, Costelytra zealandica* and *Lissorhoptrus oryzophilus.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Hylemyia spp. and Liriomyza spp.

From the order of the Siphonaptera, for example, *Xenopsylla cheopis* and Ceratophyllus spp.

From the order of the Arachnida, for example, *Scorpio maurus, Latrodectus mactans, Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Hemitarsonemus spp. and Brevipulpus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp. and Bursaphelenchus spp.

They can be employed particularly successfully for controlling plant-damaging insects, such as, for example, against the larvae of the mustard beetle (*Phaedon cochleaviae*), the green peach aphid (*Myzus persicae*) and also plant-damaging nematodes, such as, for example *Meloidogyne incognita.*

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can as such or in their formulations also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of mixing components are the following:
Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyidithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS ,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl{2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyclopene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae*, Metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoat, oxamyl, oxydemethon M,

*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, suiprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyiidazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5] dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, for example against Candida species such as *Candida albicans, Candida glabrata*, Epidermophyton species, such as *Epidermophyton floccosum*, Aspergillus species such as *Aspergillus niger* and *Aspergillus fumigatus*, Trichophyton species such as *Trichophyton mentagrophytes*, Microsporon species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

When used as insecticides, the active compounds according to the invention can furthermore be present, in their commercial formulations and in the use forms prepared from these formulations, as a mixture with synergists. Synergists are compounds which enhance the activity of the active compounds, without it being necessary for the added synergist to be active itself.

The content of active compound in the use forms prepared from the commercial formulations can vary within wide ranges. The concentration of active compound of the use forms can be from 0.0000001 to 95% by weight of active compound and is preferably between 0.0001 and 1% by weight.

Application is carried out in a manner appropriate for the use forms.

When used against hygiene pests and pests of stored products, the active compound has excellent residual activity on wood and clay and good alkali stability on limed substrates.

PREPARATION EXAMPLES

Example 1

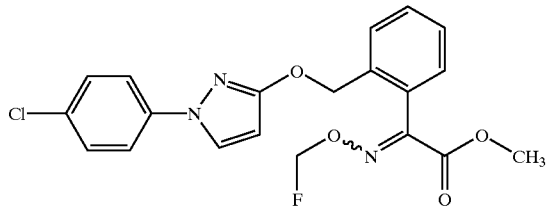

5.3 g (0.0275 mol) of 1-(4-chlorophenyl)-1,2-dihydro-3H-pyrazol-3-one, 10 g (0.0275 mol) of methyl 2-[2-(bromomethyl)phenyl]-2-[(fluoromethoxy)imino]acetate (84% pure) and 1.1 g (0.0275 mol) of sodium hydride (60%) in 40 ml of dry dimethyl formamide are stirred at room temperature for 18 hours. The solvent is then distilled off under reduced pressure. The residue is taken up in 50 ml of ethyl acetate and washed repeatedly with water. The organic phase is dried over sodium sulphate and concentrated under reduced pressure. The residue is chromatographed on silica gel using hexane/acetone (8:2). This gives 5 g (43.5% of theory) of methyl 2-[2-({[1-(4-chlorophenyl)-1H-pyrazol-3-yl]oxy}methyl)phenyl]-2-[(fluoromethoxy)imino]acetate.

HPLC: logP=3.86

Example 2

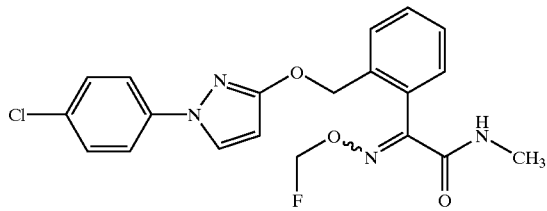

4 g (0.007 mol) of methyl 2-[2-({[1-(4-chlorophenyl)-1H-pyrazol-3-yl]oxy}methyl)-phenyl]-2-[(fluoromethoxy)imino]acetate are dissolved in 30 ml of methanol, and about 0.7 g (0.02 mol) of methylamine is then introduced, whereupon the temperature of the solution increases to about 30° C. This mixture is stirred at room temperature for 18 hours, and the solvent is then distilled off under reduced pressure. The residue is taken up in 50 ml of ethyl acetate and washed repeatedly with water. The organic phase is dried over sodium sulphate and again concentrated under reduced pressure. The residue is chromatographed on silica gel using hexane/acetone (8:2). This gives 1.8 g (60.5% of theory) of 2-[2-({[1-(4-chlorophenyl)-1H-pyrazol-3-yl]oxy}methyl)phenyl]-2-[(fluoromethoxy)imino]-N-methylacetamide.

HPLC: logP=3.30

The compounds of the formula (I-a) listed in Table 1 below are obtained analogously to Examples 1 and 2 and in accordance with the details given in the general process descriptions.

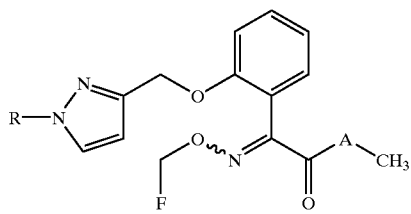

(I-a)

TABLE 1

| Example | R | A | logP |
|---|---|---|---|
| 2 | 4-chlorophenyl | NH | 3.30 |
| 3 | 4-fluorophenyl | NH | 2.91 |
| 4 | 4-(i-propyl)phenyl | O | 4.38 |
| 5 | 3-bromophenyl | NH | 3.39 |
| 6 | 4-bromophenyl | NH | 3.4 |
| 7 | 3,5-dichlorophenyl | NH | 3.93 |
| 8 | 2-chlorophenyl | O | 3.53 |
| 9 | 4-cyanophenyl | O | 3.18 |
| 10 | 4-tolyl | O | 3.74 |
| 11 | 2,4-dichlorophenyl | O | 4.09 |
| 12 | 2-bromophenyl | O | 3.54 |
| 13 | 4-bromophenyl | O | 3.98 |
| 14 | phenyl | O | 3.4 |
| 15 | 3,5-dichlorophenyl | O | 4.52 |
| 16 | 3-bromophenyl | O | 3.98 |
| 17 | 4-fluorophenyl | O | 3.47 |
| 18 | phenyl | NH | 2.83 |
| 19 | 2,4-dichlorophenyl | NH | 3.5 |
| 20 | 2,4-dichloro-4-trifluoromethylphenyl | O | 4.19 |
| 21 | 4-t-butylphenyl | O | 4.63 |
| 22 | 2-chlorophenyl | NH | 2.96 |
| 23 | 4-t-butylphenyl | NH | 4.04 |
| 24 | 2,4-dichloro-4-trifluoromethylphenyl | NH | 3.62 |
| 25 | 2-fluorophenyl | O | 3.51 |
| 26 | 2,4-difluorophenyl | O | 3.52 |
| 27 | 2,3-dichlorophenyl | O | 3.9 |
| 28 | 3,4-dimethylphenyl | O | 3.92 |
| 29 | 2,5-dichlorophenyl | O | 4.5 |
| 30 | 3-tolyl | O | 3.73 |
| 31 | 3-tolyl | NH | 3.15 |
| 32 | 2-fluorophenyl | NH | 2.93 |
| 33 | 2,4-difluorophenyl | NH | 3.02 |
| 34 | 2,3-dichlorophenyl | NH | 3.31 |
| 35 | 3,4-dimethylphenyl | NH | |
| 36 | 2,5-dichlorophenyl | NH | 3.43 |
| 37 | 3-chlorophenyl | O | 3.88 |
| 38 | 4-(i-propyl)phenyl | NH | 3.83 |
| 39 | 4-methylphenyl | O | 3.74 |
| 40 | 4-cyanophenyl | O | 3.18 |
| 41 | 4-methylphenyl | NH | 3.14 |
| 42 | 4-cyanophenyl | NH | 2.64 |
| 43 | 3-chlorophenyl | NH | 3.3 |

The logP values were determined in accordance with EEC Directive 79/831 Annex V.A8 by HPLC (gradient method, acetonitrile/0.1% aqueous phosphoric acid).

USE EXAMPLES

Example A

Erysiphe Test (barley)/protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

In this test, the substance according to the invention listed in Example (2) exhibits, at an application rate of 250 g/ha, an efficacy of 98% or more.

Example B

Puccinia Test (wheat)/protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of Puccinia recondita. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, the substance according to the invention listed in Example (1) exhibits, at an application rate of 250 g/ha, an efficacy of 98% or more.

Example C

Puccinia Test (wheat)/curative

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of Puccinia recondita. The plants remain in an incubation cabin at 20° C. and 100% relative atmospheric humidity for 48 hours. The plants are then sprayed with the preparation of active compound at the stated application rate.

The plants are placed in a greenhouse at a temperature of about 20° C. and a relative atmospheric humidity of about 80% to promote the development of rust pustules.

Evaluation is carried out 10 days after the inoculation. 0% means an efficacy which corresponds to that of the control, whereas an efficacy of 100% means that no infection is observed.

In this test, the substance according to the invention is given in Example (2) exhibits, at an application rate of 250 g/ha, an efficacy of 98% or more.

Example D

Plasmopara Test (Grape vine)/protective

| Solvent; | 24.5 parts by weight of acetone |
| --- | --- |
|  | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, the young plants are sprayed with the preparation of active compound at the stated application rate. After the spray coating has dried on, the plants are inoculated with an aqueous spore suspension of *Plasmopara viticola* and then remain in an incubation cabinet at about 20° C. and 100% relative atmospheric humidity for 1 day. The plants are then placed in a greenhouse at about 21° C. and about 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substances according to the invention listed in the Examples (1, 2, 3, 4, 5, 6, 7, 8, 11, 13, 14, 15, 16, 17, 18, 19, 26, 27, 28 and 31) exhibit, at an application rate of 100 g/ha, an efficacy of 95% or more.

Example E

Sphaerotheca Test (cucumber)/protective

| Solvent; | 24.5 parts by weight of acetone |
| --- | --- |
|  | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

In this test, the substances according to the invention listed in the Examples (1, 2, 3, 4, 5, 6, 7, 8, 11, 13, 14, 15, 16, 17, 18, 19, 26, 27, 28 and 31) exhibit, at an application rate of 100 g/ha, an efficacy of 93% or more.

Example F

Venturia Test (apple)/protective

| | |
|---|---|
| Solvent: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and about 100% relative atmospheric humidity for 1 day.

The plants are then placed in a greenhouse at about 21° C. and relative atmospheric humidity of about 90%.

Evaluation is carried out 12 days after the inoculation. 0% means an efficacy which corresponds to that of the control, whereas an efficacy of 100% means that no infection is observed.

In this test, the substances according to the invention listed in the Examples (1, 2, 3, 4, 5, 6, 7, 8, 11, 13, 14, 15, 16, 17, 18, 19, 26, 27, 28 and 31) exhibit, at an application rate of 10 g/ha, an efficacy of 98% or more.

Example G

Pyricularia Test (rice)/protective

Solvent: 25 parts by weight of N,N-dimethylacetamide

Emulsifier: 1.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound at the stated application rate. After the spray coating has dried on, the plants are inoculated with an aqueous spore suspension of *Pyricularia oryzae* and then remain at 100% rel. atmospheric humidity and 26° C. for 24 h. The plants are then placed in a greenhouse at 80% rel. atmospheric humidity and a temperature of 26° C.

Evaluation is carried out 7 days after the inoculation. 0% means an efficacy which corresponds to that of the control, whereas an efficacy of 100% means that no infection is observed.

In this test, the substances according to the invention listed in Examples (1, 2) exhibit, at an application rate of 125 g/ha, an efficacy of 60% or more.

Example H

Alternaria Test (tomato)/protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and then remain at 100% rel. atmospheric humidity and 26° C. for 24 h. The plants then remain at 96% rel. atmospheric humidity and a temperature of 20° C.

Evaluation is carried out 7 days after the inoculation. 0% means an efficacy which corresponds to that of the control, whereas an efficacy of 100% means that no infection is observed.

In this test, the substances according to the invention listed in Examples (1, 2) exhibit, at an application rate of 750 g/ha, an efficacy of 80% or more.

Example I

*Leptosphaeria nodorum* Test (wheat)/protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young wheat plants are sprayed with the preparation of active compound at the stated application rate. 1 day after the treatment, the plants are inoculated with an aqueous spore suspension of *Leptosphaeria nodorum* and then remain at 100% rel. atmospheric humidity and 20° C. for 48 h. The plants are then placed in a greenhouse at 80% rel. atmospheric humidity and a temperature of 22° C.

Evaluation is carried out 12–14 days after the inoculation. 0% means an efficacy which corresponds to that of the control, whereas an efficacy of 100% means that no infection is observed.

In this test, the substances according to the invention listed in Examples (1, 2) exhibit, at an application rate of 750 g/ha, an efficacy of 94% or more.

Example J

Phaedon Larvae Test

Solvent: 30 parts by weight of acetone

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, the substance according to the invention listed in Example (1) exhibits, at a concentration of active compound of 1000 ppm, a kill rate of 100%.

Example K

Myzus Test

Solvent: 30 parts by weight of acetone

Emulsifier: 1 part by weight of alkylaryl polyglycol ether

To produce a suitable preparation of active compound, 1 part by weight of active compound is mixed with the stated amounts of solvent and emulsifier, and the stated amount of emulsifier, and the concentrate is diluted with emulsifier-containing water to the desired concentrations.

Broad bean seedlings (*Vicia faba*) infested by the green peach aphid (*Myzus persicae*) are dipped into a preparation of active compound of the desired concentration and placed in a dish made of plastic.

After the desired period of time, the kill in % is determined. 100% means that all animals have been killed; 0% means that none of the animals have been killed.

In this test, the substance according to the invention listed in Example (1) exhibits, at a concentration of active compound of 1000 ppm, a kill rate of 95%.

What is claimed is:

1. A compound of the Formula (I),

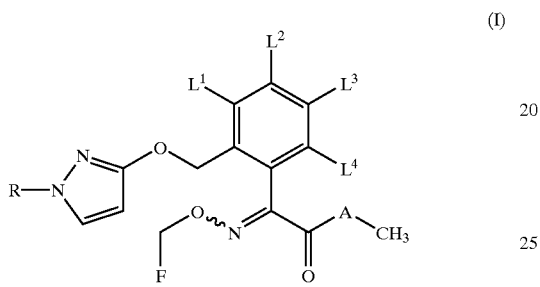

wherein
A represents oxygen or —NH—,
R represents in each case optionally substituted alkyl, cycloalkyl or aryl, $L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

2. The compound of the Formula (I) according to claim 1, wherein
A represents oxygen or —NH—, or
R represents alkyl having 1 to 8 carbon atoms, represents cycloalkyl having 3 to 7 carbon atoms which is optionally mono- or disubstituted by halogen, alkyl or hydroxyl;
or represents phenyl or naphthyl, each of which is optionally mono- to tetrasubstitued by identical or different substituents, where the substituents are optionally selected from the group consisting of:
halogen, cyano, nitro, amino, hydroxyl, formyl, carboxyl, carbamoyl, thiocarbamoyl;
in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl, having 1 to 6 carbon atoms in the respective hydrocarbon chains;
cycloalkyl or cycloalkyloxy having in each case 3 to 6 carbon atoms;
in each case doubly attached alkylene having 3 or 4 carbon atoms, oxyalkylene having 2 or 3 carbon atoms or dioxyalkylene having 1 or 2 carbon atoms, each of which radicals is optionally mono- to tetra-substituted by identical or different substituents selected from the group consisting of fluorine, chlorine, oxo, methyl, trifluoromethyl and ethyl;
or a group

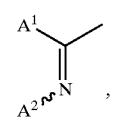

wherein
$A^1$ represents hydrogen, hydroxyl or alkyl having 1 to 4 carbon atoms or cycloalkyl having 3 to 6 carbon atoms and
$A^2$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms,
and phenyl, phenoxy, phenylthio, benzoyl, benzoylethenyl, cinnamoyl, heterocyclyl or phenylalkyl, phenylalkyloxy, phenylalkylthio, or heterocyclylalkyl having in each case 1 to 3 carbon atoms in the respective alkyl moities, each of which radicals is optionally mono- to trisubstituted in the ring moiety by halogen and/or straight-chain or branched alkyl or alkoxy having 1 to 4 carbon atoms,
$L^1$, $L^2$, $L^3$ and $L^4$ are identical or different and independently of one another each represents hydrogen, halogen, cyano, nitro, or represents alkyl, alkoxy, alkylthio, alkylsulphinyl or alkylsulphonyl having in each case 1 to 6 carbon atoms, each of which radicals is optionally substituted by 1 to 5 halogen atoms.

3. The compounds of the Formula (I) according to claim 1, wherein
A represents oxygen or —NH—,
R represents methyl, ethyl, n- or i-propyl, n-, i-, s- or t-butyl, pentyl or hexyl, or represents cyclopentyl or cyclohexyl, each of which is optionally mono- or disubstituted by fluorine, chlorine, methyl, ethyl or hydroxyl;
or represents phenyl or naphthyl, each of which is optionally mono- to tetrasubstituted by identical or different substituents, where the substituents are optionally selected from the group consisting of:
fluorine, chlorine, bromine, iodine, cyano, nitro, amino, hydroxyl, formyl, carboxyl, carbamoyl, thiocarbamoyl,
methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methyl-pentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl, methoxy, ethoxy, n- or i-propoxy, methoxymethyl, ethoxymethyl, methylthio, ethylthio, n- or i-propylthio, methylsulphinyl, ethylsulphinyl, methylsulphonyl or ethylsulphonyl, methylthiomethyl, ethylthiomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl, in each case doubly attached propanediyl, ethyleneoxy, methylenedioxy, ethylenedioxy, each of which is optionally mono- to tetrasubstituted by identical or different substituents selected from the group consisting of fluorine, chlorine, oxo, methyl and trifluoromethyl, or a grouping

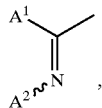

wherein $A^1$ represents hydrogen, methyl or hydroxyl and $A^2$ represents hydroxyl, methoxy, ethoxy, amino, methylamino, phenyl, benzyl or hydroxyethyl, and phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the ring moiety by halogen and/or straight-chain or branched alkyl or alkoxy having 1 to 4 carbon atoms, and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

4. The compounds of the Formula (I) according to claim 1, wherein

A represents oxygen or —NH—, or

R represents phenyl which is optionally mono- or disubstituted by identical or different substituents, where the substituents are optionally selected from the:

cyano, fluorine, chlorine, bromine, methyl, ethyl, n- or i-propyl, n-, i-, s- or t-butyl, trifluoromethyl, $L^1$ and $L^3$ represent hydrogen and $L^2$ and $L^4$ independently of one another represent hydrogen or methyl.

5. A process for preparing the compound of the Formula (I) as defined in claim 1, comprising the step of:

a) reacting a compound of the Formula (II)

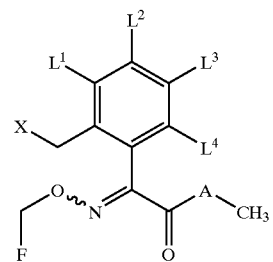

(II)

wherein

A, $L^1$, $L^2$, $L^3$ and $L^4$ are as defined in claim 1 and

X represents halogen, with a compound of the Formula (III),

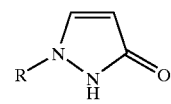

(III)

wherein

R is as defined in claim 1, optionally in the presence of a diluent and optionally in the presence of an acid acceptor, or that b) a compound of the Formula (I) wherein A is oxygen, is reacted with methylamine, optionally in the presence of a diluent.

6. A composition for controlling harmful organisms, comprising one or more extenders and/or carriers and, optionally, surfactants, and at least one compound as defined in claim 1.

7. A method for controlling harmful organisms, comprising the step of allowing an effective amount of a compound as defined in claim 1 to act on harmful organisms and/or their habitat.

8. A process for preparing a composition as defined in claim 6, comprising the step of mixing a compound as defined therein with one or more extenders and/or carriers and/or surfactants.

* * * * *